United States Patent [19]

Foster

[11] Patent Number: 4,560,794

[45] Date of Patent: Dec. 24, 1985

[54] PROCESS FOR PREPARING METHOXYTRIFLUOROMETHYLNAPHTHOIC ACID FROM METHYLNAPHTHOIC ACID

[75] Inventor: Arthur M. Foster, Lewiston, N.Y.

[73] Assignee: Occidental Chemical Corporation, Niagara Falls, N.Y.

[21] Appl. No.: 667,184

[22] Filed: Nov. 1, 1984

[51] Int. Cl.$^4$ .............................................. C07C 63/34
[52] U.S. Cl. .................................. 562/467; 562/427; 562/444; 562/450; 260/544 B; 560/56; 560/100
[58] Field of Search ........................ 562/467; 560/56; 260/544 B

[56] References Cited

PUBLICATIONS

Fung et al., Canad. Journal of Chem., vol. 61, pp. 368–371 (1982).

Primary Examiner—Paul J. Killos
Attorney, Agent, or Firm—James F. Tao; William G. Gosz

[57] ABSTRACT

A multi-step process is described for preparing a methoxytrifluoromethylnaphthoic acid of formula

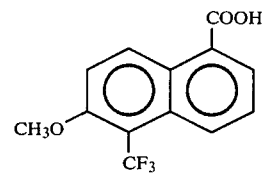

from 1-methyl-5-naphthoic acid and for preparing novel intermediate compounds of formula

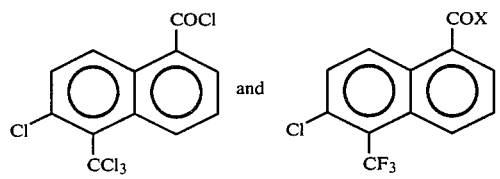

where X is chlorine or fluorine.

Methoxytrifluoromethylnaphthoic acid is useful for preparing biologically active compounds such as naphthyl thioamide derivatives which inhibit aldose reductase activity.

20 Claims, No Drawings

PROCESS FOR PREPARING METHOXYTRIFLUOROMETHYLNAPHTHOIC ACID FROM METHYLNAPHTHOIC ACID

BACKGROUND OF THE INVENTION

This invention relates to a novel process and intermediates for preparing a methoxytrifluoromethylnaphthoic acid compound of formula

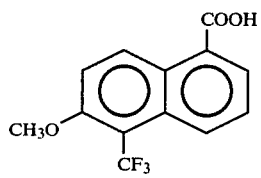

from 1-methyl-5-naphthoic acid. The methoxytrifluoromethylnaphthoic acid of the present invention, which is designated as 2-methoxy-1-trifluoromethyl-5-napthoic acid, is useful as a chemical intermediate for the synthesis of various end-products. In particular, one such end-product is a therapeutic agent having efficacy for inhibiting aldose reductase activity in human tissues. This compound, which is a naphthyl thioamide compound of formula

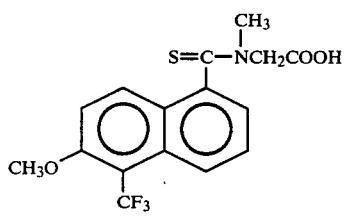

is currently being evaluated for such efficacy. This is a proprietary compound of the Ayerst Research Laboratories and is designated by the trademark Tolrestat. Tolrestat is believed to inhibit the aldose reductase enzyme in human cells which converts glucose into sorbitol. Excessive sorbitol production in humans is a condition common to a large number of diabetics, and has been linked to chronic complications among diabetics such as blindness, hypertension, pain and discomfort. See *Chemical & Engineering News,* page 5 (Sept. 5, 1983).

The cost of Tolrestat is presently quite high due in part to the high cost of the raw materials used in manufacturing this drug. One of the primary raw materials is the methoxytrifluoromethylnaphthoic acid of the present invention.

Various methods are disclosed in the prior art for preparing 2-methoxy-1-trifluoromethyl-5-naphthoic acid. Thus, it is known to react a mixture of iodine and iodic acid with 6-methoxy-1-naphthalenecarboxylic acid methyl ester in a mixture of acetic acid and sulfuric acid to prepare 5-iodo-6-methoxy-1-naphthalenecarboxylic acid methyl ester. This compound can then be reacted with trifluoromethyl iodide in pyridine in the presence of copper powder and subsequently hydrolyzed in a mixture of sodium hydroxide and methanol to prepare 2-methoxy-1-trifluoromethyl-5-naphthoic acid. Alternatively, the 5-iodo-6-methoxy-1-naphthalenecarboxylic acid methyl ester can be reacted with a mixture of copper, mercuric thiofluoride, and cuprous thiomethyltrifluoride (CuSCF$_3$) in dimethylformamide, and subsequently hydrolyzed in a mixture of 2-methoxyethanol and sodium hydroxide to prepare the target compound. These procedures are described in more detail in examples 1f, 1h and 63 of European Patent Application No. 59,596, published Sept. 8, 1982.

Fung et al in the *Canadian Journal of Chemistry,* Vol. 61, pp. 368–371 (1982) describe the preparation of 1-trifluoromethyl-2-naphthalenols from 3-chloropropyltoluene. The 3-chloropropyltoluene is reacted with magnesium, a catalytic amount of iodine and a suspension of lithium trifluoroacetate in anhydrous ether to prepare the corresponding ketone. The ketone is then used to prepare a ketone-oxime by reaction with potassium nitrate in water and acetic acid. The ketone-oxime is then reacted with concentrated sulfuric acid to close the ring, and subsequently hydrolyzed with concentrated hydrochloric acid to prepare the hydroxyketone. The hydroxyketone is dehydrated by reaction with thionyl chloride, 4-dimethylaminopyridine and pyridine, and subsequently methylated with dimethylsulfate to prepare 2-methoxy-5-methyl-1-trifluoromethylnaphthalene, the methyl analog of the carboxylic acid compound of the present invention.

As is evident from the foregoing, prior art processes for preparing methoxytrifluoromethylnaphthoic acid or analogous compounds suffer from numerous disadvantages. These processes are cumbersome, involve expensive reactants and/or reagents and processing techniques, and are not readily adaptable for commercial production. It will be readily apparent to those skilled in the art, therefor, that a need exists to develop an improved process for preparing methoxytrifluoromethylnaphthoic acid using readily available and inexpensive raw materials and commercially feasible processing techniques. One such process utilizing 1,5-dimethylnaphthalene as a starting material is disclosed in a commonly assigned copending application filed of even date herewith. The present application is directed to an alternate process utilizing 1-methyl-5-naphthoic acid as a starting material.

SUMMARY OF THE INVENTION

In accordance with this invention, a process for preparing 2-methoxy-1-trifluoromethyl-5-naphthoic acid from 1-methyl-5-naphthoic acid comprises the steps of:
(a) converting 1-methyl-5-naphthoic acid into 2-chloro-1-methyl-5-naphthoyl chloride,
(b) photochlorinating the 2-chloro-1-methyl-5-naphthoyl chloride in the liquid phase to prepare 2-chloro-1-trichloromethyl-5-naphthoyl chloride,
(c) fluorinating the 2-chloro-1-trichloromethyl-5-naphthoyl chloride in the liquid phase in the presence of a halogen transfer catalyst to prepare 2-chloro-1-trifluoromethyl-5-naphthoyl halide,
(d) esterifying the 2-chloro-1-trifluoromethyl-5-naphthoyl halide by reaction with a lower alkanol to prepare 2-chloro-1-trifluoromethyl-5-naphthalate,
(e) methoxylating the 2-chloro-1-trifluoromethyl-5-naphthalate by reaction with sodium methoxide in the presence of a cuprous halide to prepare 2-methoxy-1-trifluoromethyl-5-naphthalate, and
(f) hydrolyzing the 2-methoxy-1-trifluoromethyl-5-naphthalate.

The intermediate compounds prepared according to steps (b) and (c) are novel naphthoyl halides which can be represented by the formulas

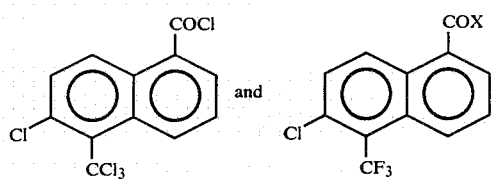

where X is chlorine or fluorine.

DETAILED DESCRIPTION OF THE INVENTION

The process of the present invention is a multi-stage reaction sequence for preparing a methoxytrifluoromethylnaphthoic acid compound of formula

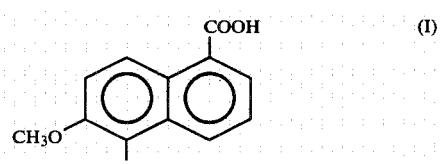
(I)

from 1-methyl-5-naphthoic acid. The methoxytrifluoromethylnaphthoic acid compound of formula (I) is designated as 2-methoxy-1-trifluoromethyl-5-naphthoic acid in accordance with accepted nomenclature. 1-Methyl-5-naphthoic acid is a known compound which can be obtained from commercial sources.

The first step of the process is the conversion of 1-methyl-5-naphthoic acid into 2-chloro-1-methyl-5-naphthoyl chloride. This conversion can proceed according to either of the following reaction schemes:

(1)

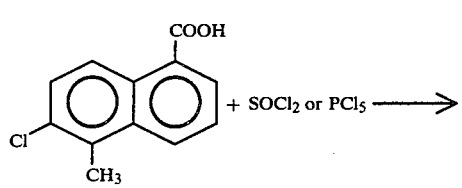

OR

(2)

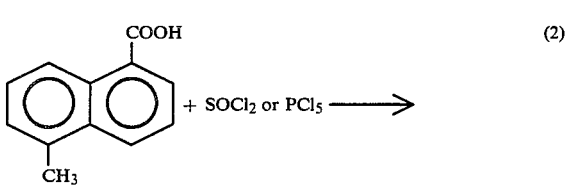

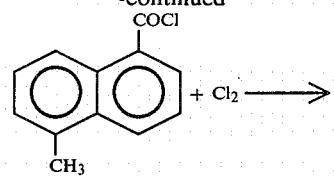

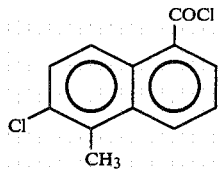

The ring chlorination phase of reactions (1) or (2) can be conducted in the presence of a solvent. Suitable solvents include halogenated aromatic compounds such as carbon tetrachloride. In a preferred embodiment, chlorine is employed as the chlorinating agent and a Lewis acid catalyst, such as antimony pentachloride, is used as a chlorination catalyst. Although other chlorinated isomers will be formed during ring chlorination, these isomers can be separated using well-known separatory techniques such as distillation and solvent extraction. Temperature and pressure conditions are not critical and can vary over wide limits.

The naphthoic acid can be converted to the corresponding acid chloride in reactions (1) or (2) using a suitable reagent such as thionyl chloride or phosphorus pentachloride.

The 2-chloro-1-methyl-5-naphthoyl chloride is then reacted with chlorine in a photochlorination reaction to chlorinate the methyl group and prepare 2-chloro-1-trichloromethyl-5-naphthoyl chloride in accordance with the following reaction.

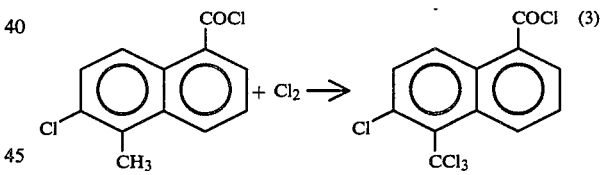
(3)

Reaction (3) is a liquid phase photochlorination reaction which is preferably conducted in a halogenated organic solvent such as carbon tetrachloride. Process conditions for this reaction are also not critical and a wide range of temperature and pressure conditions can be used. The product of reaction (3) is a novel compound.

The 2-chloro-1-trichloromethyl-5-naphthoyl chloride is then reacted with a fluorinating agent in the presence of a halogen transfer catalyst to prepare 2-chloro-1-trifluoromethyl-5-naphthoyl in accordance with the following reaction.

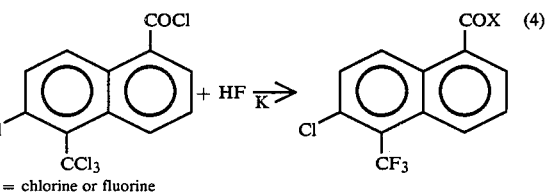
(4)

X = chlorine or fluorine

Reaction (4) is also conducted in the liquid phase in the presence of a halogen transfer catalyst. Such catalysts are well-known in the literature and include, for example, ferric chloride, aluminum chloride, titanium tetrachloride, antimony pentafluoride, antimony pentachloride, and the like. The preferred catalyst is antimony pentachloride. The fluorination process can be conducted over a wide range of process conditions and either with or without a solvent. Suitable solvents include DMF, benzene, nitrobenzene, and the like. A preferred fluorinating agent is hydrogen fluoride which is suitably employed in a three molar excess. Other isomers will be produced by this reaction in varying amounts, but these isomers can be separated from the final product using standard separatory techniques.

The products of reaction (4) are also novel compounds. The acid fluoride generally results from the use of amounts of hydrogen fluoride in excess of three moles.

The 2-chloro-1-trifluoromethyl-5-naphthoyl halide is then reacted with a lower alkanol to prepare 2-chloro-1-trifluoromethyl-5-naphthalate as shown below.

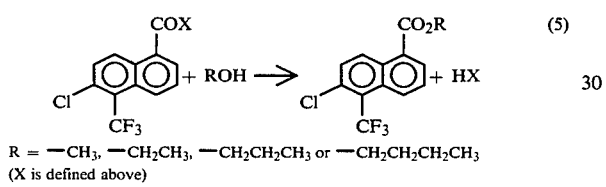

R = —CH$_3$, —CH$_2$CH$_3$, —CH$_2$CH$_2$CH$_3$ or —CH$_2$CH$_2$CH$_2$CH$_3$
(X is defined above)

The lower alkanol employed in the esterification reaction (5) is preferably methanol, although other alkanols such as ethanol, propanol and butanol can also be successfully used in this process. The expression "lower alkanol" is therefore intended to include all of these alcohols.

The 2-chloro-1-trifluoromethyl-5-naphthalate is then reacted with sodium methoxide in the presence of a cuprous halide, preferably cuprous chloride, to prepare 2-methoxy-1-trifluoromethyl-5-naphthalate as shown below.

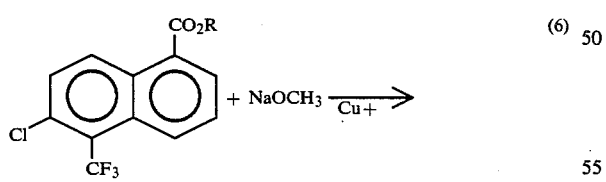

(R is defined above)

The reaction sequence of this invention is completed upon hydrolyzing the 2-methoxy-1-trifluoromethyl-5-naphthalate as shown below.

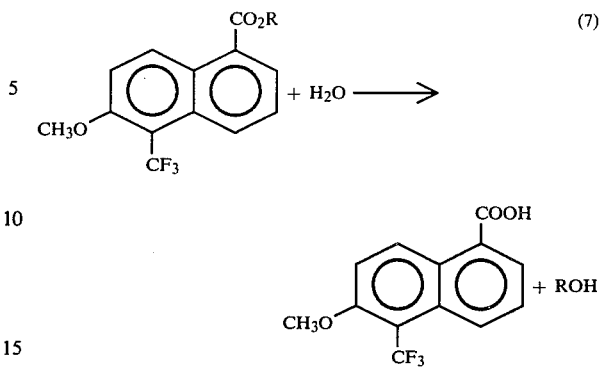

The final hydrolysis reaction (7) can be either acid or base catalyzed. A base catalyzed reaction can be conducted in an aqueous solution of methanol and an alkali metal hydroxide such as sodium hydroxide or potassium hydroxide.

The methoxytrifluoromethylnaphthoic acid produced according to this process can be employed in combination with N-methylglycine to prepare an amidoacid of formula

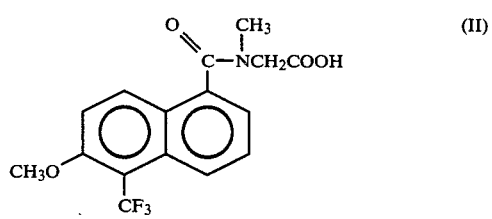

The amidoacid can be easily converted into a naphthyl thioamide compound of formula

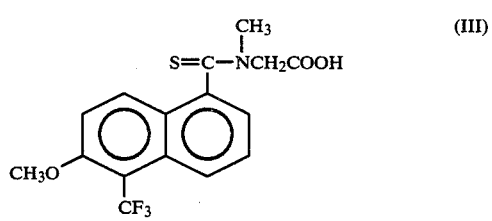

by reaction with phosphorus pentasulfide. This latter compound III is a useful therapeutic agent for the treatment of diabetic side-effects.

What is claimed is:

1. A process for preparing a methoxytrifluoromethylnaphthoic acid compound of formula

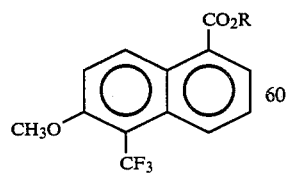

comprising the steps of
(a) converting 1-methyl-5-naphthoic acid into a chloromethylnaphthoyl chloride compound of formula

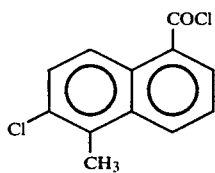

(b) photochlorinating the chloromethylnaphthoyl chloride of step (a) in the liquid phase to prepare a chlorotrichloromethylnaphthoyl chloride of formula

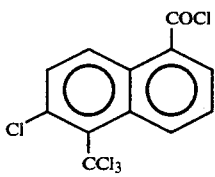

(c) fluorinating the chlorotrichlormethylnaphthoyl chloride of step (b) in the liquid phase in the presence of a halogen transfer catalyst to prepare a chlorotrifluoromethylnaphthoyl halide of formula

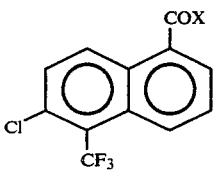

where X is chlorine or fluorine, (d) esterifying the chlorotrifluoromethylnaphthoyl halide of step (c) by reaction with a lower alkanol to prepare a chlorotrifluoromethylnaphthalate of formula

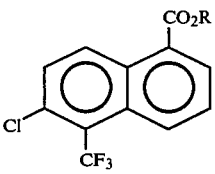

where R is methyl, ethyl, propyl or butyl, (e) methoxylating the chlorotrifluoromethylnaphthalate of step (d) by reaction with sodium methoxide in the presence of a cuprous halide to prepare a methoxytrifluoromethylnaphthalate of formula

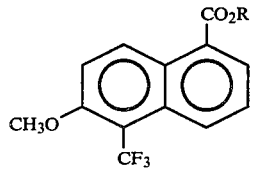

where R is defined in step (d), and (f) hydrolyzing the methoxytrifluoromethylnaphthalate of step (e).

2. The process of claim 1 wherein the 1-methyl-5-naphthoic acid in step (a) is first chlorinated in the liquid phase to prepare a chloromethylnaphthoic acid compound of formula

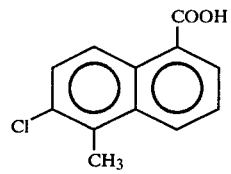

and subsequently reacted with thionyl chloride or phosphorus pentachloride to prepare a chloromethylnaphthoyl chloride compound of formula

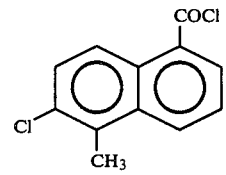

3. The process of claim 2 wherein the ring chlorination is conducted in a solvent.

4. The process of claim 3 wherein the solvent is CCl₄.

5. The process of claim 2 wherein the ring chlorination is conducted in the presence of a catalytic amount of a Lewis acid catalyst.

6. The process of claim 5 wherein the chlorinating agent is chlorine and the Lewis acid catalyst is antimony pentachloride.

7. The process of claim 1 wherein the 1-methyl-5-naphthoic acid in step (a) is first reacted with thionyl chloride or phosphorus pentachloride to prepare a methylnaphthoyl chloride compound of formula

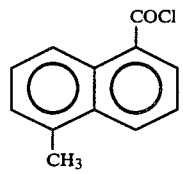

and subsequently chlorinated in the liquid phase to prepare a chloromethylnaphthoyl chloride compound of formula

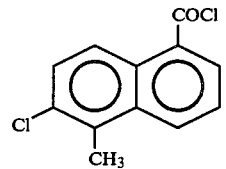

8. The process of claim 7 wherein the ring chlorination is conducted in a solvent.

9. The process of claim 8 wherein the solvent is CCl₄.

10. The process of claim 7 wherein the ring chlorination is conducted in the presence of a catalytic amount of a Lewis acid catalyst.

11. The process of claim 10 wherein the chlorinating agent is chlorine and the Lewis acid catalyst is antimony pentachloride.

12. The process of claim 1 wherein the photochlorination in step (b) is conducted in a halogenated solvent.

13. The process of claim 12 wherein the halogenated solvent is CCl$_4$.

14. The process of claim 1 wherein the fluorinating agent is hydrogen fluoride.

15. The process of claim 14 wherein the halogen transfer catalyst is antimony pentachloride.

16. The process of claim 1 wherein the lower alkanol in step (d) is methanol and the cuprous halide is cuprous chloride.

17. The process of claim 16 wherein the hydrolysis in step (f) is conducted in an aqueous solution of an alkali metal hydroxide and methanol.

18. The process of claim 17 wherein the alkali metal hydroxide is sodium hydroxide.

19. A compound of formula

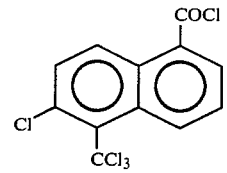

20. A compound of formula

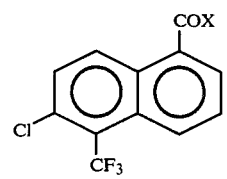

where X is chlorine or fluorine.

* * * * *